United States Patent
Soula et al.

(10) Patent No.: US 6,694,178 B1
(45) Date of Patent: Feb. 17, 2004

(54) METHOD AND DEVICE FOR REPRESENTING AND MONITORING FUNCTIONAL PARAMETERS OF A PHYSIOLOGICAL SYSTEM

(75) Inventors: Anatoli Soula, Moscow Region (RU); Youri Kitachine, Moscow Region (RU); Werner Gillessen, Strausberg (DE)

(73) Assignee: Energy-Lab Technologies GmbH, Hamburg (DE)

( * ) Notice: Subject to any disclaimer, the term of this patent is extended or adjusted under 35 U.S.C. 154(b) by 0 days.

(21) Appl. No.: 09/600,354

(22) PCT Filed: Jan. 12, 1999

(86) PCT No.: PCT/DE99/00080

§ 371 (c)(1),
(2), (4) Date: Oct. 3, 2000

(87) PCT Pub. No.: WO99/35558

PCT Pub. Date: Jul. 15, 1999

(30) Foreign Application Priority Data

Jan. 12, 1998 (DE) .......................................... 198 01 240

(51) Int. Cl.$^7$ .............................................. A61B 5/044
(52) U.S. Cl. ................................................... 600/523
(58) Field of Search ................................ 600/523, 512, 600/522, 506, 509

(56) References Cited

U.S. PATENT DOCUMENTS

| 5,215,099 A | 6/1993 | Haberl et al. ................ 128/702 |
| 5,458,116 A | 10/1995 | Egler .......................... 128/710 |
| 5,803,084 A | * 9/1998 | Olson .......................... 600/512 |

FOREIGN PATENT DOCUMENTS

| DE | 195 23 199 | 1/1997 |
| WO | WO 91/19452 | 12/1991 |

OTHER PUBLICATIONS

L. Moura et al., "A Microcomputer–Based Cardiac Mapping System for Recurrent Ventricular Tachycardia Surgery", Proceedings of Computer in Cardiology 1992, Durham, NC, USA; pp. 431–434.

B. H. Branham et al., "A system for Accurate Interactive 3–D Display of Cardiac Electrical Activity", Proceedings of Computer in Cardiology 1992, Durham, NC, USA; pp. 335–338.

M.R. Young et al., "A Real–Time Data Acquisition System for the Display of Three Dimensional Cardiac Activation Maps", Proceedings of Computer in Cardiology 1992; Durham, NC, USA; pp. 331–334.

A. Calderon et al., "3–D Mapping of Body Surface Potentials"; Medical Informatics, Apr.–Jun. 1987; UK, vol. 12, No. 2, pp. 125–135.

R.W. Brancato et al., "Computer Analysis of EKG Tracings for the Detection of Latent Coronary Artery Disease", Society of Engineering Science, Inc., Engineering Science in Biomedicine, 7$^{th}$ Annual Meeting, Washington University, St. Louis, MO, 1970.

* cited by examiner

Primary Examiner—George R. Evanisko
(74) Attorney, Agent, or Firm—Christie, Parker & Hale, LLP

(57) ABSTRACT

The invention relates to a method and a device for representing and monitoring function parameters of a physiological system, in particular electrocardiographic data, which are derived from electronic measuring signals. The object of the present invention is to provide a method and a device which quickly and in a fashion which can be used by anyone render it possible to analyze the variation in process states and to predict future states. This object is achieved according to the invention by virtue of the fact that the data are combined to form a basic data model and are converted into a graphical portrait which is constructed in the manner of a three-dimensional topological model.

14 Claims, 14 Drawing Sheets

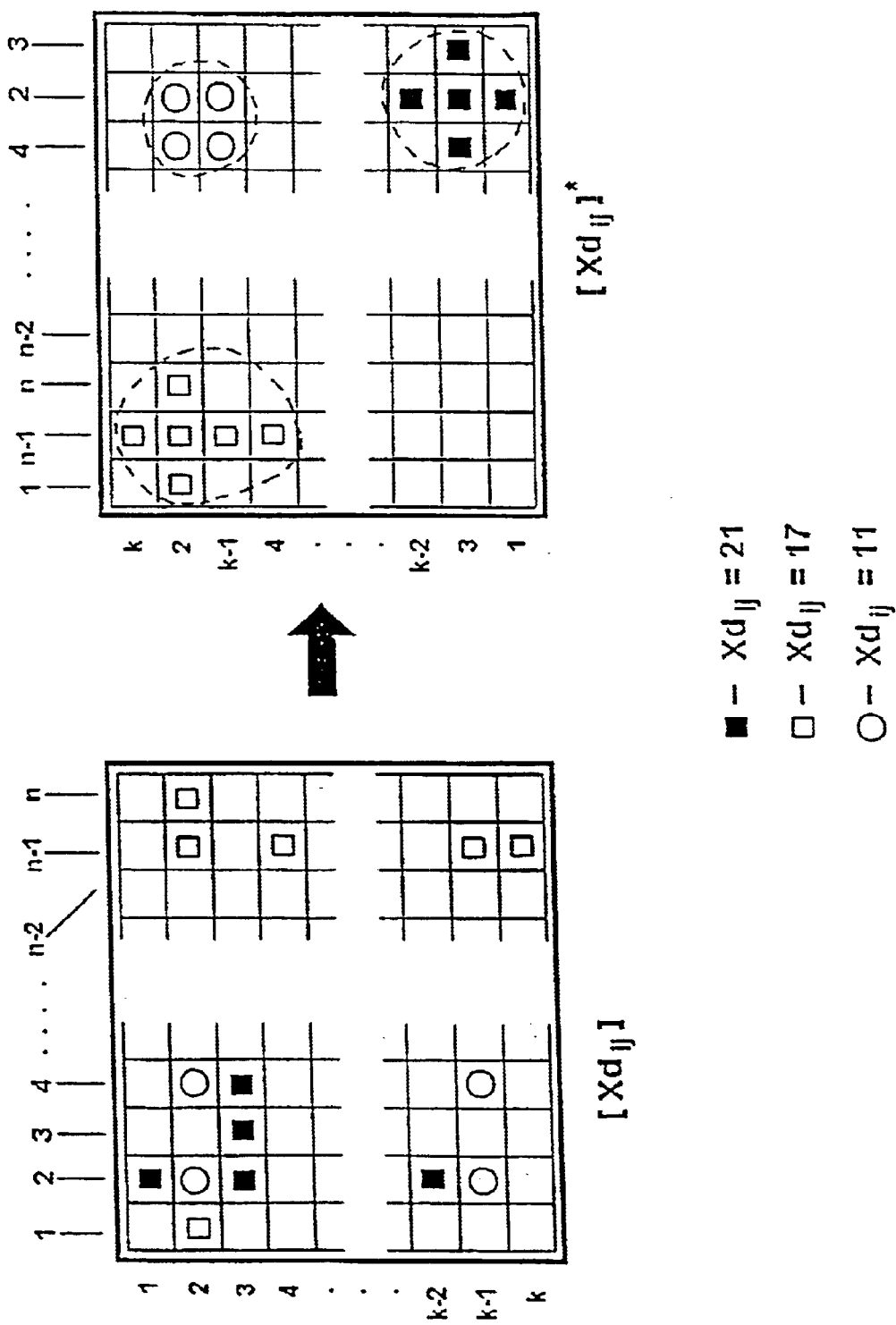

METHOD AND DEVICE FOR REPRESENTING AND MONITORING FUNCTIONAL PARAMETERS OF A PHYSIOLOGICAL SYSTEM

The invention relates to a method and a device for representing and monitoring function parameters of a physiological system, in particular electrocardiographic data, which are derived from electronic measuring signals.

Since the discovery of the action currents of the heart in 1887, data determined have been recorded using electrocardiography. After the initial use of the string galvanometer in conjunction with a paper strip with a light-sensitive coating for the purpose of detecting the action potentials, recording measuring units have been in use for several decades. In these measuring units, recording means comparable to a plotter execute a linear movement as a function of the amplified measured values, a paper strip being guided along perpendicular to the movement of the recording means and below the latter.

This produces a curve which has a typical, periodically repeating characteristic. With the aid of this curve, an educated and trained cardiologist can detect changes in the impulse formation, dysrhythmias or damage to the heart muscle. A disadvantage of this type of representation is that, particularly in the case of small changes, the information content can be detected only with difficulty, and that special training and wide experience are required to interpret the curves. Furthermore, a not inconsiderable period is required for careful evaluation of an electrocardiogram.

In the further development, the curve was represented on a display screen, and this rendered possible a substantially refined representation, since the electron beam has a lesser inertia than the recording unit, and therefore operates virtually without delay. A brief representation of the curve and the limited resolution on the display screen are disadvantageous here.

The two-dimensional representation led to the development of vector cardiography, in which the action currents of the heart muscle fibers are recorded in such a way that loops are produced in the three planes in space, only trained specialist staff being capable of carrying out interpretation of the space curves.

U.S. Pat. No. 5,215,099 discloses a device and a method for predicting cardiac dysrhythmias, in the case of which a multiplicity of ECG measurements of the QRS region are averaged, and atypical waveforms are rejected. The average values of the ECG measurements are subsequently digitized, the segments are shifted in time relative to one another, analyzed and transformed by means of a Fourier transformation. The transformed data are expressed in a three-dimensional form, it being possible to infer a low risk of infarct when the temporally displaced segments correspond to one another.

Various methods for representing surface potentials are described in the articles "A microcomputer-based cardiac mapping system for tachycardia surgery"; Moura et al., "A system for accurate interactive 3-D display of cardiac electrical activity" Branham et al., "A real-time data acquisition system for the display of three dimensional cardiac activation maps"; Young et al., and "3-D mapping of body surface potentials"; Calderon et al.; although they permit positionally accurate assignment of the measuring points their evaluation requires experience, however.

The object of the present invention is to provide a method and device which quickly and in a fashion which can be used by anyone render it possible to analyze the variation in process states and to predict future states.

This object is achieved according to the invention by means of a method in accordance with claim 1 and a device in accordance with claim 17.

The word information microscope is illustrative both of the method according to the invention and of the device for carrying it out, since available information which is not immediately available to a viewer is brought to human perception. In the case of a light microscope, very small structures of matter are rendered visible by refraction of the light waves in a lens system. The information microscope provides function parameters of a physiological system in such a way that these are made acceptable per se to general perception, and that extremely small variations become clear.

The interpretation of complex information such as is contained, for example, in an ECG is substantially simplified and accelerated by the method according to the invention. Frequent data acquisition is possible because of the very short measuring period and the simple application, with the result that it is possible to observe a variation in a physiological system by measuring at short intervals over a long period.

The short evaluation period and the simple interpretability of the measured values provided also reveal very small variations. Predictions relating to the physiological system under investigation are possible in conjunction with the possibility of qualitatively estimating the measured values represented.

Conversion into a graphical portrait produces an individual mapping of the system under investigation with the aid of which identification is possible, as in the case of a photograph.

The graphical portrait is advantageously constructed in the manner of a three-dimensional topological model, since it is possible to transmit the highest information density with the aid of this representation, which comes closest to the natural perception of the environment. Thus, even complex measured values can be represented in a way which is graphic and easily accessible. Likewise, small deviations which could be identified only with difficulty in a two-dimensional diagram become perceptible through this type of representation because of the larger information quantity. Like a map, in which the topological conditions are visualized by an appropriate arrangement, the three-dimensional model conveys a view of the function parameters with great vividness and a high information density.

The digitization of the data permits regions previously plotted longitudinally to be assigned to space coordinates, thus achieving a three-dimensional effect. Starting from a significant measured variable, specific sections of the measured value characteristic are assigned specific spatial areas. The analog signal is digitized, and the value is used, as a function of its temporal occurrence, as an interpolation point for forming a largely closed surface. In addition, the individual interpolation points are stored with a color code which comprises both chrominance and luminance. This color code storage is performed on the basis of the measured values of in each case one analysis cycle, and permits qualitative orientation with the aid of the color values and brightness values of the image.

The analysis cycle is advantageously fixed by determining the temporal spacing of at least two repeating significant variables, the variables being a function of the physiological conditions and/or of the body part under examination. In the case of cardiological examinations, the interval between two R impulses is suggested as the length of an analysis cycle, since this is easy to determine and has a satisfactory edge steepness as a rule. The analysis cycle is fixed in this case in such a way that the significant action potentials of the heart muscle are detected, and therefore that the entire range from P to T is covered.

In order to increase the accuracy and informativeness of the measurement, and to increase the precision of the representation, it is advantageous to have a measuring period which covers a multiple of an analysis cycle. Since the discrete values of he digitized measurement correspondingly are assigned according to their sequence to specific zones inside the pictorial representation, a measurement over a time interval which contains the entire range of the values to be taken into account is favorable.

It is particularly advantageous that the assignment of color codes is calculated by combining empirically determined reference data. On the basis of data which are stored in an electronic memory and can be called up therefrom, the interpolation points are assigned information with reference to color and brightness. The assignment is performed as a function of the deviations of the measured values relative to the reference values. Depending on the extent of deviation and the position inside the curve, the measured values are assigned a corresponding color value and brightness value such that an image is produced which permits a simple diagnosis on the basis of the shape, color and brightness, because the type of information representation has been varied on the basis of medical reference data and permits simple assignment even of very small deviations.

For the purpose of not further processing evident interference signals and thereby extending the complexity of processing and reducing the accuracy of the display, a development of the invention provides a selection of the analysis cycles to be evaluated after the calculation of the autocorrelation function and of [sic] a comparison with empirically determined reference data.

In order to analyze the recorded data of an analysis cycle, they are led through a high-pass filter and digitized, and the values thus obtained are subtracted from the unfiltered data, which have likewise been digitized. The data thus obtained are combined in accordance with their value to form groups or so-called clusters such that in the case of considering a plurality of analysis circles in a time interval groups with the same value are respectively arranged adjacently in a matrix. By grouping the values, the initially irregularly distributed small fluctuations are ordered, and a regular structure with a few constant features [lacuna] from the at first glance random small fluctuations. The sequence of the grouping is individually stored for each physiological system, that is to say for each patient.

The sequence of the grouping is advantageously determined in the course of a reference measurement and applied to subsequent analysis cycles. If the renewed application of the sequence of the regrouping yields a changed structure, it is possible therefrom to infer variations in the physiological system.

In an advantageous refinement of the invention, all the analysis cycles of a time interval are taken into account when in the image calculation, since the resolution is increased by augmenting the interpolation points. The deviations present scatter the interpolation points, thus giving rise to cluster formation in the case of the evaluation of a plurality of analysis cycles.

For application in the field of individuals, in particular, it is appropriate to determine action potentials in heart examinations using a standardized 3-point recording, since a sufficient accuracy of the measurement is achieved in this way even in the case of less sensitive pick-ups. Other recordings are also provided for an application in the cardiological diagnostic field, for example the 2- or 6-point recording, the latter method delivering the most useful information on the basis of which the person skilled in the art can easily and quickly make qualitative and quantitative diagnoses.

In a development of the invention, the elimination of noise quantities is performed by correlation of the measured values of a plurality of analysis cycles. Since the occurrence of noise quantities is random in the case of recorded measured values, whereas the actual measured values are correlated with one another, the noise signals are filtered out by a correlation such that even small deviations in the image representation which would remain unrecognized in the noise in the conventional representation are detected.

In a refinement of the invention, the recorded measured values are relayed via online data lines, for example to a diagnostic center, where the data are evaluated and archived. The person to be examined need no longer be examined on the spot, but could record the data at a suitable time in the home environment, after which specialist staff evaluate them.

A development of the invention is to store the image representation with a therapy recommendation such that the dedicated interpretation of the measurement results are [sic] supported by a recommendation determined empirically.

A device with an information microscope for carrying out the method according to claim 1 has devices for data recording and conversion into electric signals, and a device for fixing an analysis cycle. Also provided is an analog-to-digital converter which digitizes the recorded data and feeds them to a storage unit. In an arithmetic unit with evaluation software connected thereto the data are provided with chrominance values and luminance values in accordance with their deviation from the data stored in the storage unit, and are assigned to a three-dimensional coordinate system. The individual values of the digitized signals form interpolation points which are connected to a closed surface. The pixels determined are conditioned for the respective output device in a control unit. The evaluation or output device transmits the image information in the form of a color picture or a color printout.

In a refinement of the information microscope, the devices for data recording are designed as electrodes, in particular as adhesive or clamping electrodes, since it is easy in this way to obtain information on action potentials of muscular activities. Precisely the clamping electrodes are easy to handle and also offer a layperson the possibility of obtaining data on a physiological system. Depending on the type of the recorded variable, use is to be made of pressure sensors, flowrate meters or optical sensors, it also being possible to use these in combination. In principle, all pick-ups which determine statements on physiological systems are suitable, the conversion into electric signals being performed as a function of the recorded measured value, for example in a pressure transducer or a photoelectric transducer.

Since the electric signals frequently have an excessively small amplitude, it is advantageous to provide an amplifier which can be used to provide a satisfactorily powerful signal.

Stored in the storage unit for the purpose of quick calculation of the topological model in the information microscope are empirically determined reference data which permit the values determined to be assigned either to previous measurements or to pathological changes, the storage unit advantageously being connected to the arithmetic unit, which is preferably designed as a computer.

Outputting at a monitor is particularly advantageous for uncomplicated provision of the topological model, a color monitor enhancing the informativeness of the model of the function parameters. Also provided as output medium are printers, in particular color printers, or other image-generating media such as imagers or projectors.

In a refinement of the device according to the invention, an interface for external transmission of data is provided, so that the measured values can be assessed, for example in a diagnostic center, without the need for the person examined to be present. This examination method is advantageous in the case of continuous monitoring, in particular.

Exemplary embodiments of the invention are explained in more detail below with the aid of the drawings, in which:

FIG. 5 shows an illustration of the principle of the regrouping of matrix values;

Figure 1:
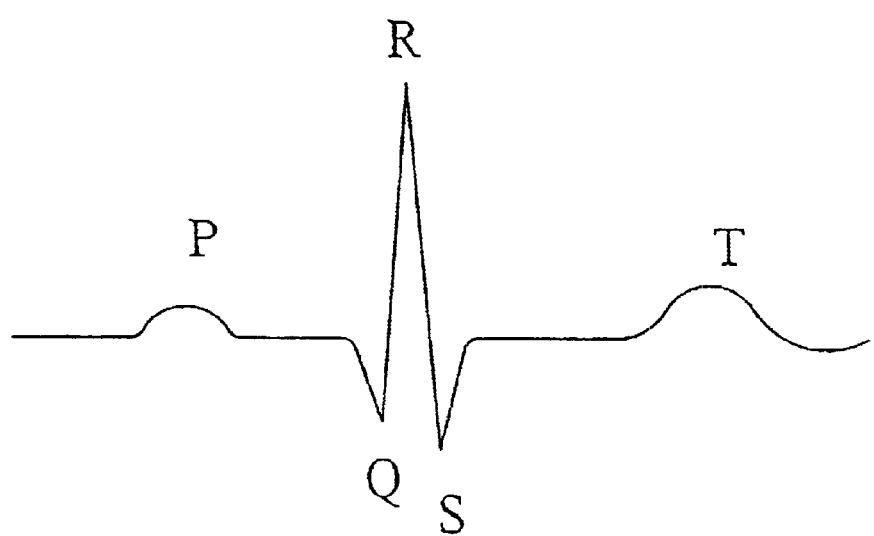
FIG. 1 shows an illustration of a normal electrocardiogram.

FIG. 1 shows a conventional electrocardiogram (ECG) in its two-dimensional illustration, in which the time axis is plotted on the abscissa and the action potentials are plotted on the ordinate. Such a normal ECG can be divided into four regions, the beginning and end of which are denoted by letters from P to T. The region from P to Q corresponds to the contraction of the atria, and that from Q to T corresponds to the contraction of the chambers of the heart. The QRS complex corresponds to the ventricular stimulus conduction in the heart chambers, and the T wave comes about through the repolarization, which proceeds differently from place to place. The QRS complex, the ST segment and the T wave together form the ventricular complex of the ECG.

Figure 2:
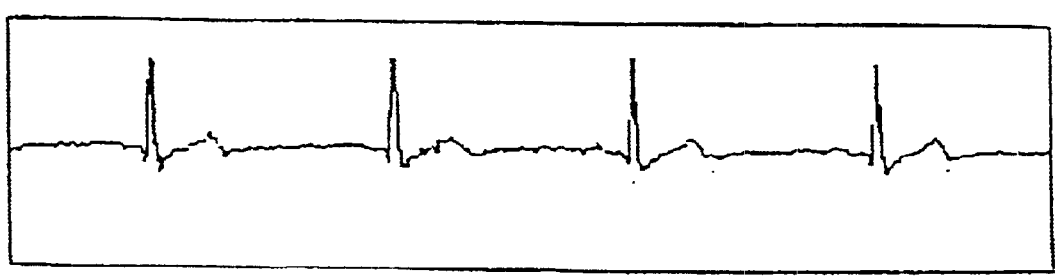
FIG. 2 shows an illustration of a patient ECG.

It may be seen with the aid of a patient ECG in FIG. 2 that the course of the curve corresponds to that of a normal ECG, no rectilinear connections occurring, however, between the respective points, but there invariably being relatively small deflections to record corresponding to the courses of the action potentials. Such an ECG can be interpreted only with the aid of experience in depth, even for a person skilled in the art. In particular, the small variations from heartbeat to heartbeat are not obvious and are easily overlooked, although the information has been detected.

Figure 3:
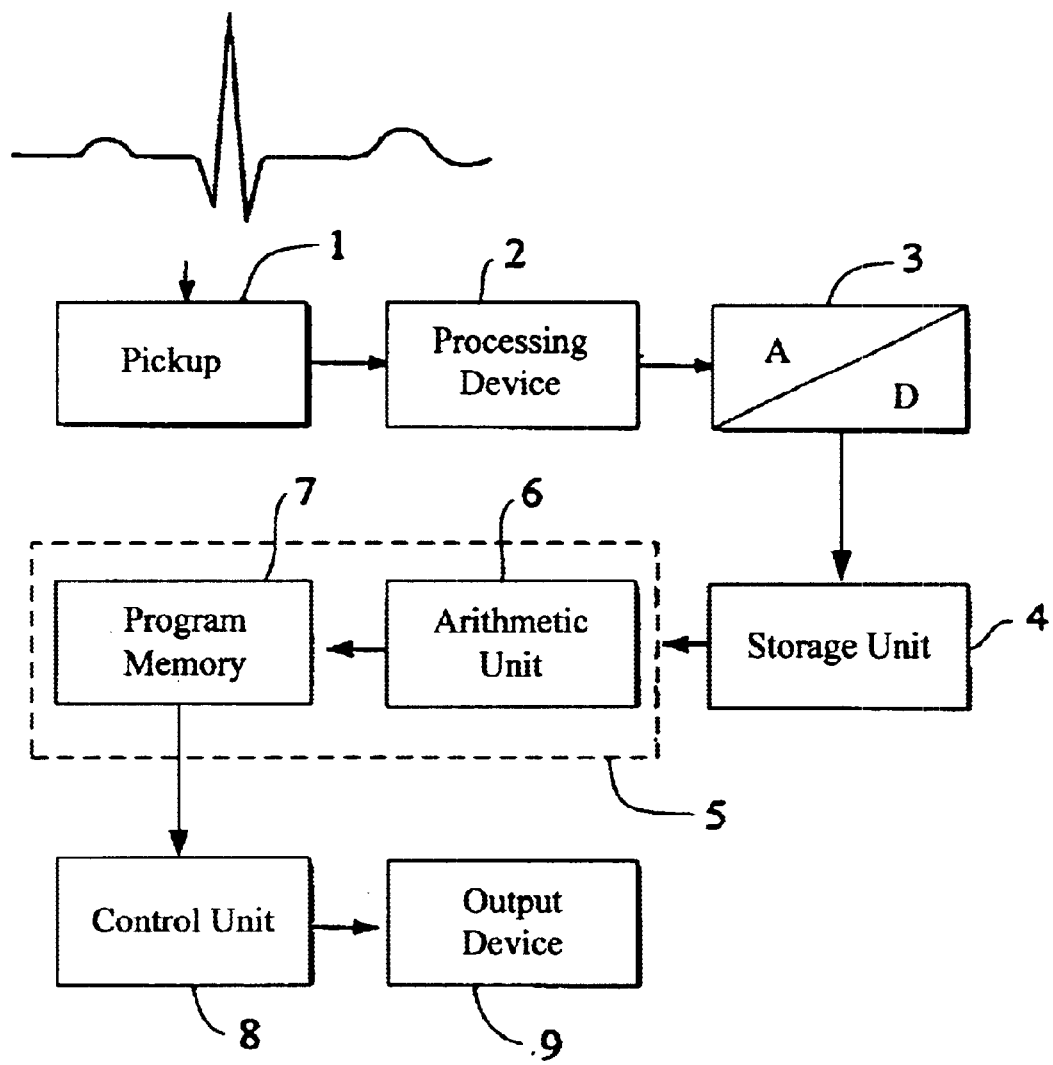
FIG. 3 shows a block diagram of the information microscope.

The block diagram in FIG. 3 illustrates the mode of procedure for a ECG measurement. The person to be examined fastens two standardized electrodes at the usual measuring points (wrist joint and/or ankle joint) and a neutral electrode at the earlobe. A triggering device (not illustrated) is used to carry out the recording of measured values for a specific time interval. The action currents are amplified in a pickup 1 and relayed to a processing device 2. A signal conversion firstly takes place if the measured values are not present in the form of electric signals.

Figure 4:
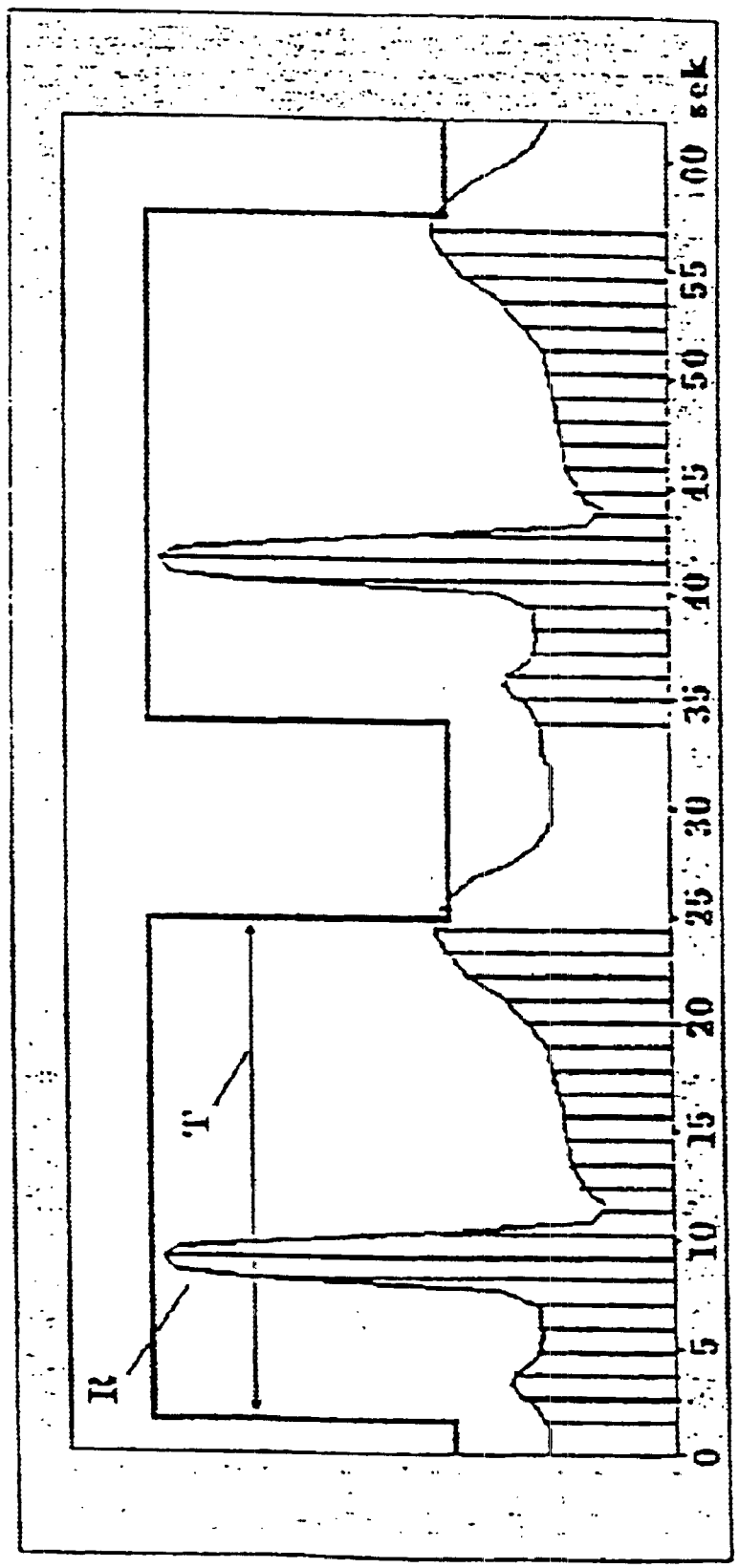
FIG. 4 shows a diagram of the formation of the analysis cycle.

The length of the analysis cycle, which is determined by the duration of two heartbeats, is fixed in the processing device 2. FIG. 4 illustrates such a fixing diagrammatically, in the case of which, starting from the interval of two successive R waves, a shortened interval is determined for the analysis cycle length T. 80–90% of the R-R interval is provided as guide value for T, the QRST complex being covered as a result. The period T thus comprises the entire ventricular complex of the ECG, and the signals present in analog form are digitized in an analog-to-digital converter 3 such that a specific number of n values are available per analysis cycle. Since the analysis cycle is calculated starting from a significant variable, in the selected example of the R wave the respective digitized values can be assigned to a specific region of the ECG.

For reasons of illustrative capability, in the example illustrated the signal is subdivided into 25 values, it also being possible, of course, to undertake a higher resolution. The number of the periods T, that is to say of the analysis cycles recorded within a measurement period, is provided with the index i. The index i runs from 1 to 60 in the case of an analysis cycle of one minute and a heart rate of one beat per second. The digitized values are fed to a storage unit 4 to which an evaluation unit 5, comprising an arithmetic unit 6 with evaluation software and a program memory 7 is connected.

Figure 4A:
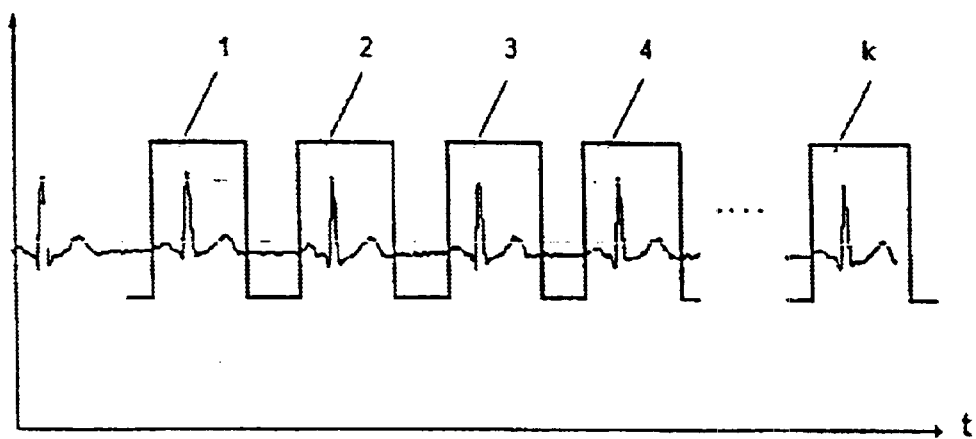
FIG. 4a shows a sequence of a plurality of ECG signals in a time interval.
Figure 4B:
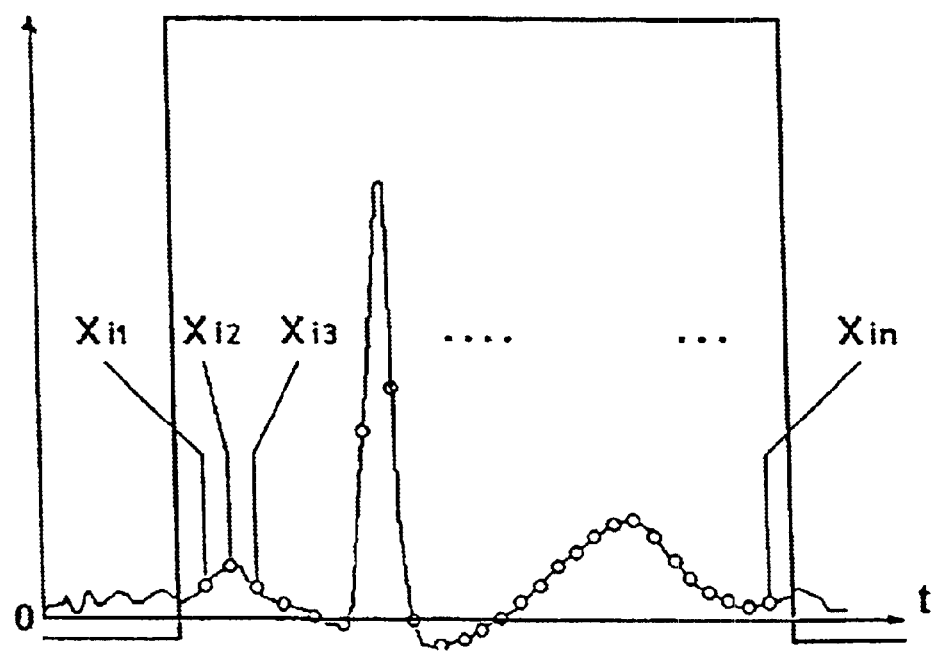
FIG. 4b shows an illustration of the digitization of an ECG signal.

An ECG measurement is plotted over a longer period in FIG. 4a, a window of length T being formed k times with the QRST complex. FIG. 4b illustrates in detail how the digitized values $X_{ij}$ are determined, the index i denoting the respective QRST complex and running from 1 to k, and the index j running from 1 to n and denoting the respective measuring point. Each of the measuring points j is assigned an X value, with the result that a matrix $X_{ij}$ with k rows and n columns is produced.

A high-pass filter is used in each QRST complex to eliminate the small fluctuations, small fluctuations being regarded as variations in the range of 0.5–1.5% from the value of the R wave. After the digitization, the high-pass filtering also yields a k×n matrix, but without small fluctuations. This matrix $Xf_{ij}$ is subtracted from the matrix $X_{ij}$, thus producing a difference matrix $Xd_{ij}$ in which only the small fluctuations are contained.

The difference matrix $Xd_{ij}$ determined is transposed in such a way that the closely situated values are combined into groups or clusters. Such a regrouping of the matrix is illustrated in FIG. 5, the left-hand matrix representing the difference matrix determined, and the right-hand matrix representing the finally regrouped matrix. The various symbols inside the matrix $Xd_{ij}$ represent equal values in each case here the values 11, 17 and 21. The matrix $Xd_{ij}$ is rearranged by successive transpositions in such a way that the respective values (illustrated here by symbols) are juxtaposed combined as far as possible into groups, as illustrated in the right-hand matrix $Xd_{ij}^*$ in FIG. 5. The respective values form so-called clusters, and the operation of regrouping or transposition is easy to detect with the aid of the altered column and row indexing. The sequence of the transpositions is different for each person, and is determined in the course of a reference measurement and stored as an individual function.

Figure 6:
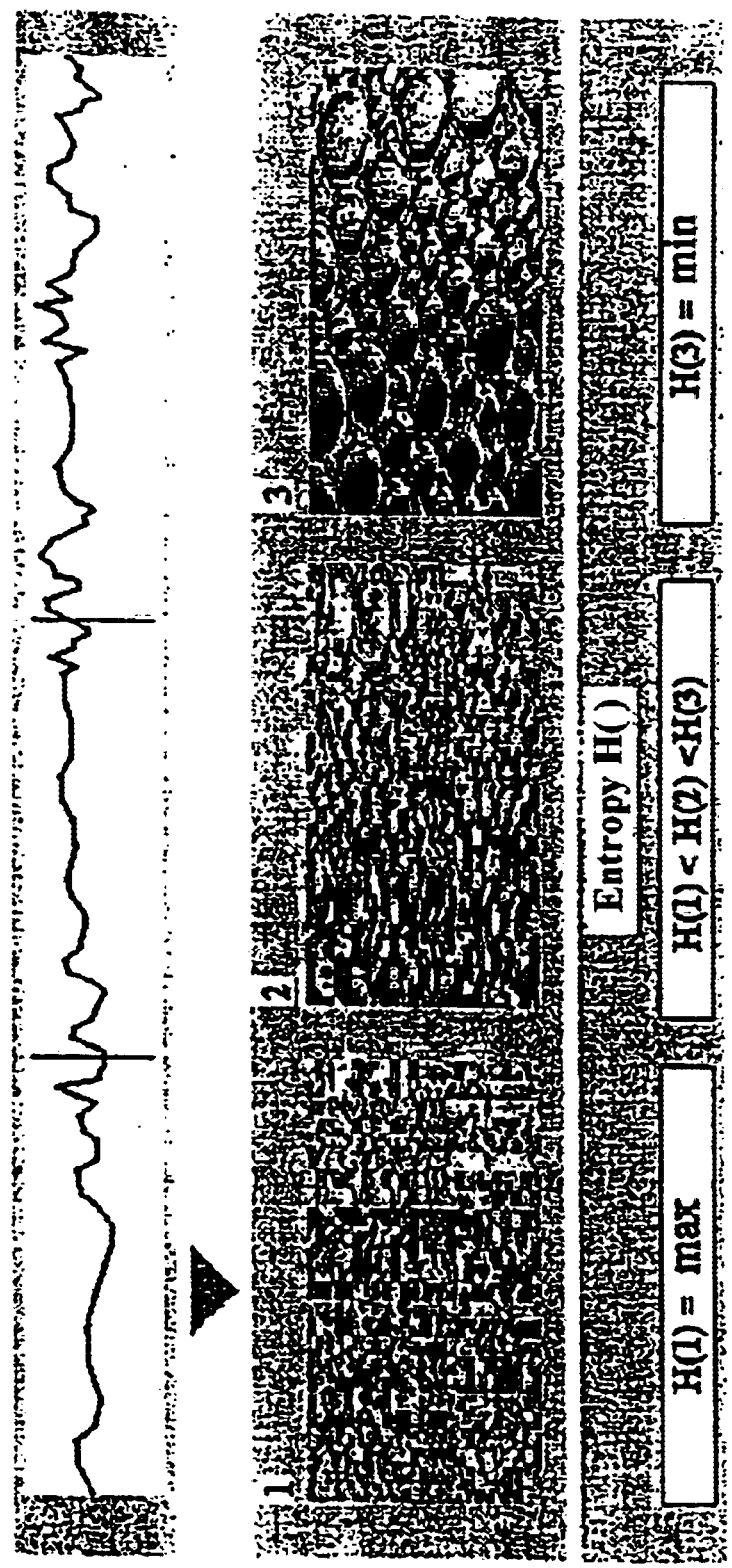
FIG. 6 shows an illustration of different phases of the regrouping of the difference matrix.

FIG. 6 shows the result of the transposition of the difference matrix with the aid of the illustrations 1 to 3, the illustration showing the initial difference matrix, that is to say the signal before the regrouping. Half the transpositions are undertaken in the illustration 2, even first clusters therefore being observed. Illustration 3 in FIG. 6 shows the final variant of the transposition, in which the respective values have been optimally combined to form clusters. The transposition of the values leads to enhanced ordering inside the difference matrix, so that it is possible also to speak of a reduction in the "information entropy" by the formation of the clusters. If a disordered state of the values is still present in illustration 1, H(1) therefore assumes a maximum value, this disorder reduces with increasing regrouping until it is finally a minimum (H(3)=min).

The transposition of the difference matrix $Xd_{ij}$ into the matrix $Xd_{ij}^*$ reveals an inner structure from the initial small fluctuations, which at first glance are random. If this structure is constant, that is to say if the same fluctuations occur at the respective points, it will be repeated at the next application of the determined sequence of transpositions of the matrix $Xd_{ij}$.

Figure 7:
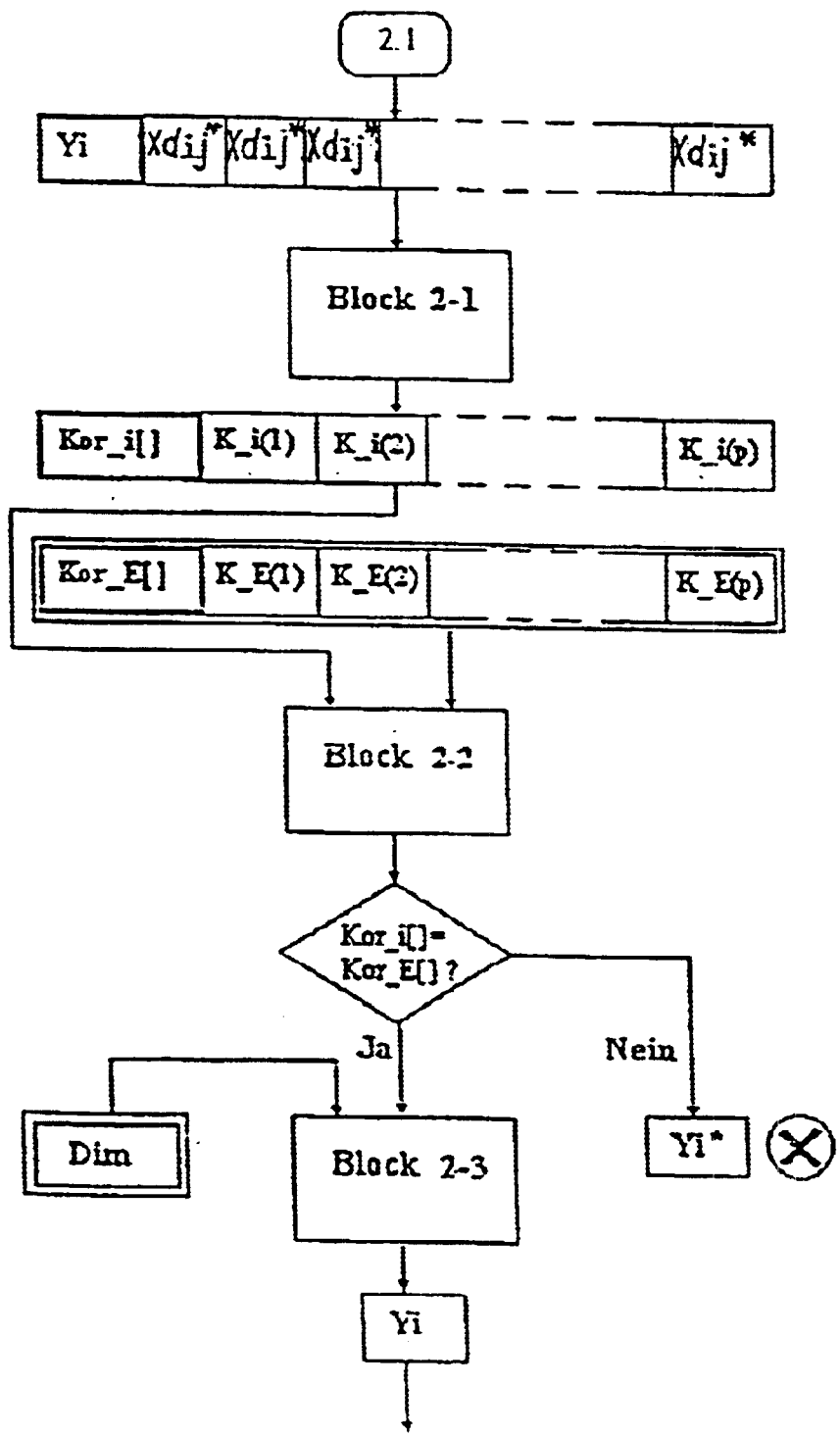
FIGS. 7 and 8 show block diagrams of the signal processing.

Processing using the evaluation software operates according to a principle illustrated as a block diagram in FIG. 7, a further procedure being used to remove the fluctuations which are unsuitable for analyzing the recorded data. The signal $Yi=Xd_{ij}^*$ (i=1, ..., k; j=1, ..., n), which depends on the other values $Xdi1^*$, $Xdi2^*$, ..., $Xdin^*$ is transmitted to the unit 2-1 in which the autocorrelation function Fkor_i of the data group is calculated. This function indicates whether a variable depends on an intrinsic value at an earlier instant, that is to say whether it contains hidden periodicities, for example. In this case, sharp maxima or minima are indicated at those points which correspond to periods or antiperiods of the process. This function is relayed to the first of the two inputs of the block 2-2.

The function Fkor_E, which is stored in the program memory 7 and is used as the standard for comparison is applied to the second input. The function Fkor_E is a measurement, adopted as reference, which is processed with reference to the autocorrelation and is set up for each examinee. On the basis of this reference measurement, the functions Fkor_i and Fkor_E are intercompared using defined criteria in unit 2-2. Since the significance of the variations in the physiological system become clear from extremely small fluctuations within the recorded signals, those signals are filtered out which have an excessively large difference relative to the reference measurement. In this way, the two functions are intercompared only within a previously fixed range. In the event of absence of similarity, that is to say given excessively large deviations of the investigated signals from the reference measurement, further processing of the signal is stopped.

If there is similarity according to the prescribed criteria, the signal Yi is further processed in unit 2-3. At a second input of unit 2-3, a magnification function Dim with a magnification factor m, which is likewise stored in the program memory 7, is applied. A signal magnified to a fixed range, that is to say a normalized signal, is produced from the signal Yi and the magnification factor. This magnified signal is subsequently relayed to unit 2-1.

Figure 8:
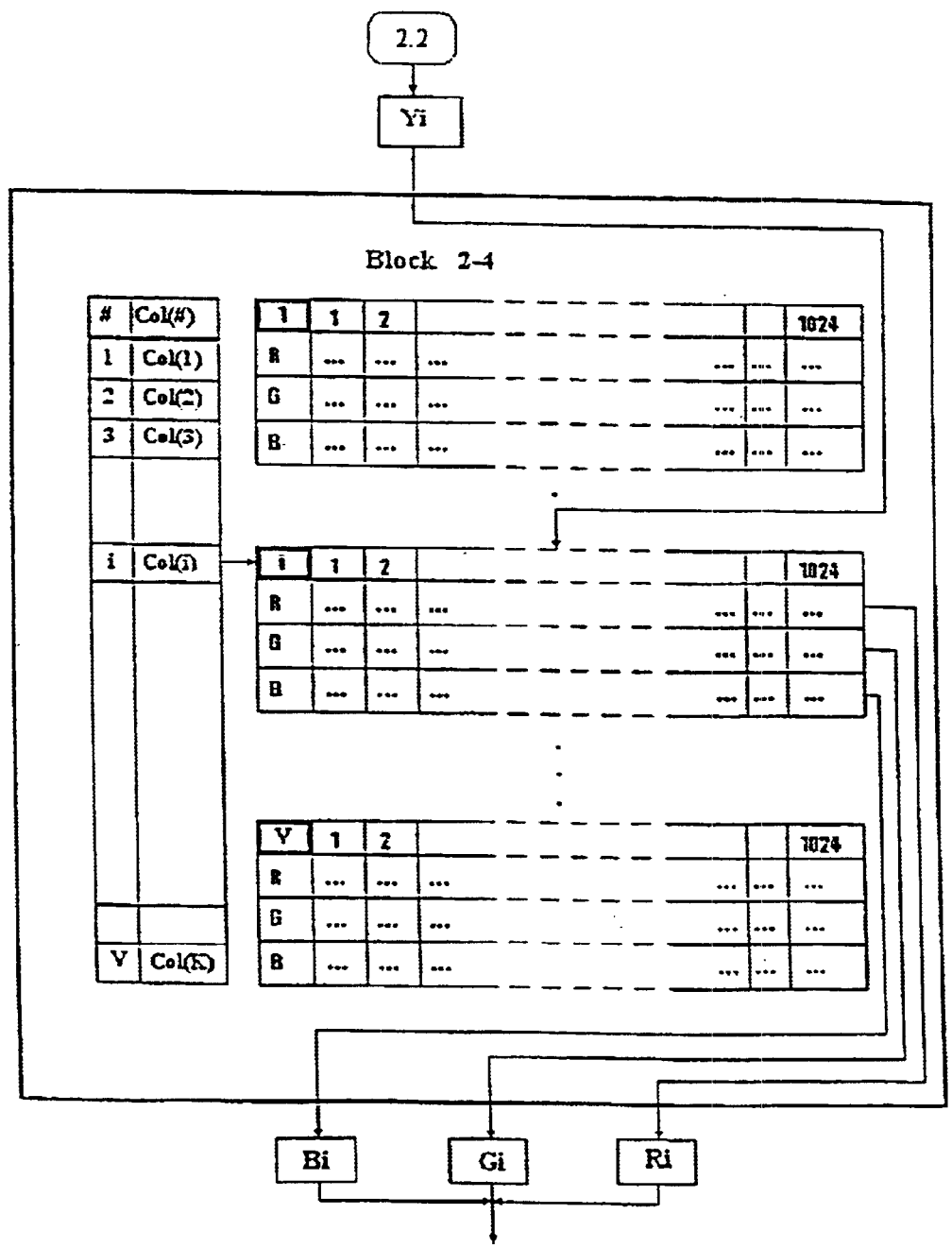

The assignment of the color code is illustrated in FIG. 8 with the aid of a block diagram. The normalized signal Yi is combined in a further step with color components which are stored in tables. These tables contain n columns and three rows, the latter corresponding to a red, (R), green (G) and blue (B), color component. 1024 values of the signal Yi are present in the selected example. Each of the 1024 values represents the value of the deviation at a specific point in the time domain T, and can therefore be assigned to a specific rage of heart muscle activity, for example the range of the S wave.

Each of these 1024 values is then assigned a color value, which is selected from a specific range of a color spectrum. The values Col(i) in the color tables are assigned to the respective signal Yi, with the result that three secondary color codes Ri, Gi and Bi are assigned to the signal Yi at the output of unit 2-4. This means that each point of the matrix $Xd_{ij}^*$ is assigned a dedicated color value; for each of the 1024 values, a color value from the components R (red), G (yellow) and B (blue) is determined from a color spectrum assigned for the respective range of a signal.

The selection from this color spectrum is performed as a function of the deviation relative to the reference curve; that is to say, a color value varies when the deviation varies. The color values are stored in tabular form in the program memory 7 and are assigned to the respective value. A reliable distinction is rendered possible in the case of very small differences by an appropriate color selection, a spectral characteristic and a matched resolution, thus effecting an enhancement of the sensitivity in the detection of very small variations.

Figure 9:
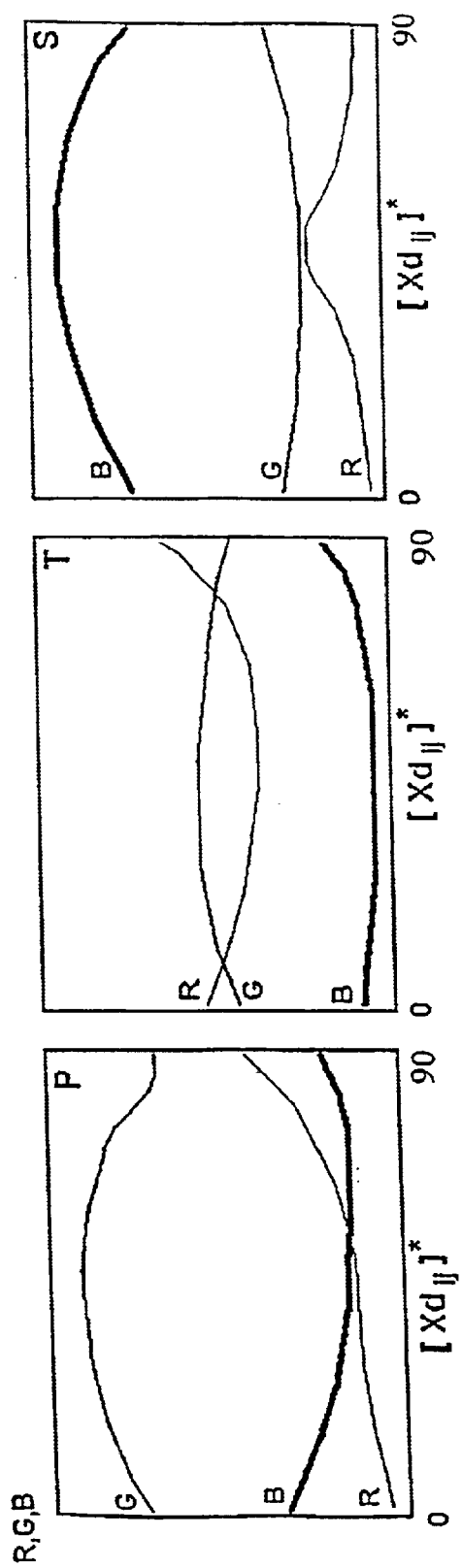
FIG. 9 shows a combination of various color spectra as a function of the abscissa values of the ECG signal.

FIG. 9 shows a diagrammatic characteristic of threecolor spectra P, T and S., which are respectively assigned to the region of the ECG signal having the same name; for example, the P region is assigned the color green, the T wave is assigned the color yellow, and the S wave is assigned the color blue. The respective characteristic of the color components yellow, red and blue is plotted on the abscissa, the selection of the abscissa values being performed as a function of the magnitude of the signal $Xd_{ij}^*$. If, for example, no deviation can be established for the range P, a color spectrum in the composition of 0 is selected. A value of 90 is provided in the case of a very large value for the deviation at the point P. Other increments are to be selected accordingly in the case of a higher resolution.

Figure 10:
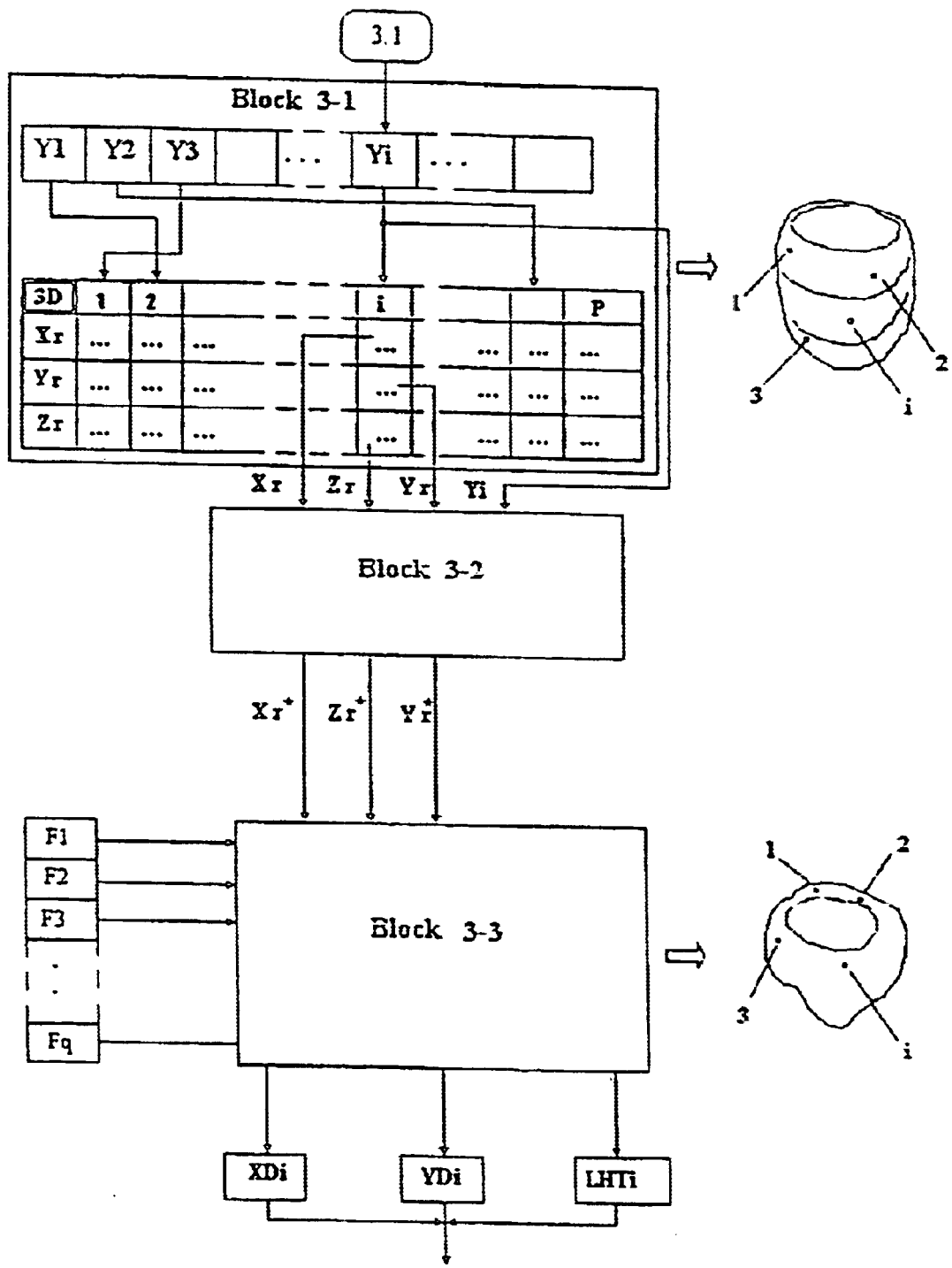
FIGS. 10 and 11 show block diagrams of the signal processing.

The further processing of the signal Yi, now provided with a color code, in unit 3-1 is illustrated in FIG. 10. Unit 3-1 contains a 3D table, stored in the program memory 7, with three rows which respectively correspond to a space dimension X, Y and Z, and p columns (p<=K, where K=number of analysis cycles). The signal Yi provided with the color code is combined with the components Xr, Yr and Zr which represent the initial coordinates for the signal Yi in a simulated space.

Here, as well, ranges of the ECG signal determined similarly to the described method of color code assignment are assigned specific spatial areas of a previously fixed basic model or basic body. Depending on the magnitude of the value Yi, a value deviating from the basic model is assigned for the space coordinates Xr, Yr and Zr. The space coordinates deviating from the basic model are used to produce an individual image that reproduces the smallest fluctuations in the recorded signal. A portrait of the examined heart is therefore produced which reproduces the variations in the ECG signal of a patient as an individual illustration which varies in shape and color depending on the measured variations.

The coordinates Xr, Yr and Zr are relayed to three inputs of unit 3-2 on whose fourth input the signal Yi is present. In a fashion similar to that in the case of the method described in the case of color assignment, the coordinates $Xr^*$, $Yr^*$ and $Zr^*$ are formed from these variables:

$$Xr^* = Xr - F\_X(Yi)$$

$$Yr^* = Yr - F\_Y(Yi)$$

$$Zr^* = Zr - F\_Z(Yi)$$

The coordinates Xr*, Yr* and Zr* thus determined are projected onto a surface in unit 3-3, with the result that the 3D animation can be output on a display screen or a printer. A moving illustration on a monitor is also possible given appropriate equipment. In addition to the coordinates, signals Fl to Fq which, for example, prescribe information on the position of the observer, parameters of the output system or the objective focus, are present at unit 3-3 in addition to the coordinates.

The signals are assigned a vertical and horizontal component (YDi and XDi) [lacuna] a luminance function (LHTI) at the output of unit 3-3, in order to permit a pictorial representation.

Figure 11:
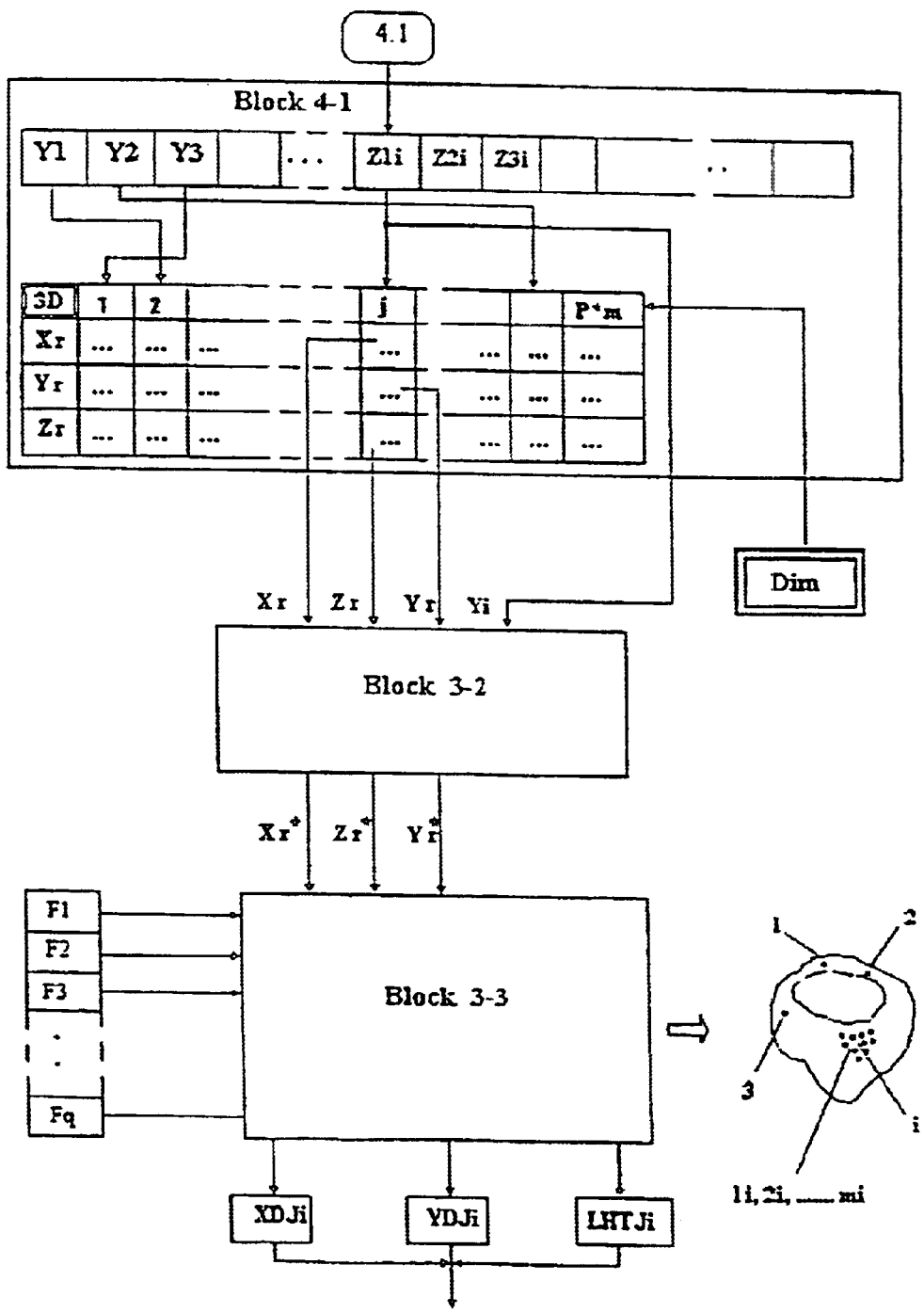

The determination of the image values in the environment of the interpolation points, which runs in principle according to the method for assigning space coordinates in the unit 3-1 is illustrated in FIG. 11 in a block diagram. The intermediate values (Zli, Z2i . . . Z) required for a closed surface representation are determined in a fashion similar to the methods described above, the 3D table being enlarged by the magnification factor m on the basis of the p columns in block 3-1 in FIG. 10, that is to say p*m columns are present. The interpolation between the respective points is performed using known algorithms, in the simplest case by linear interpolation. This interpolation is illustrated diagrammatically in the lower right of FIG. 11, where the pixels li to mi are illustrated around the point i. The remaining interpolated points around the other interpolation points are determined correspondingly.

The respective functions for calculating the values, that is to say which color values are assigned to the respective signal value, in the way the space coordinates are calculated relative to the respective value, or which brightness values are prescribed, are stored in the program memory 7 and determined on the basis of empirical investigations. The calculation of the space coordinates and the assignment of the brightness values is [sic] performed in parallel.

Figure 12:
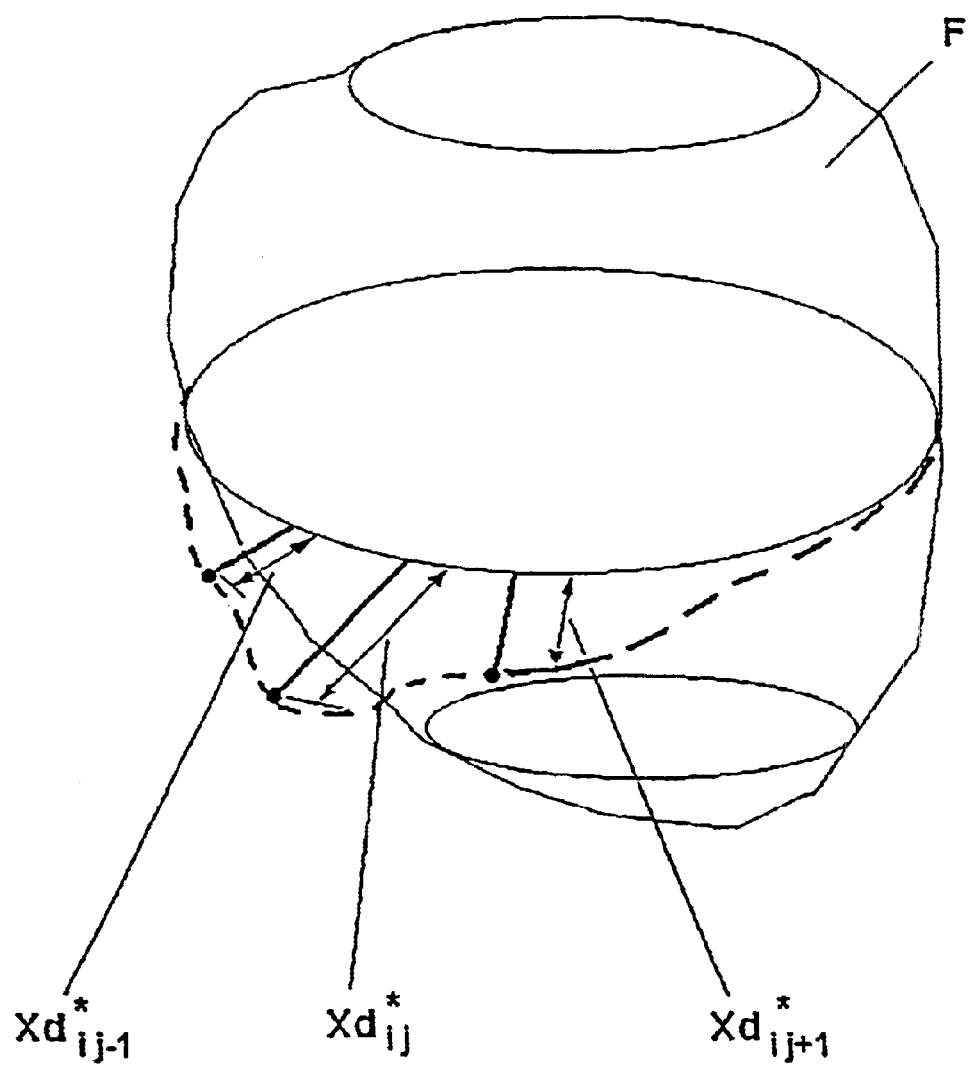
FIG. 12 shows an illustration of the principle of the assignment of interpolation points to space coordinates.

FIG. 12 shows a diagrammatic illustration of the space coordinate assignment in a selected plane. Starting from a basic model F, new space coordinates are assigned on the basis of the calculated values $Xd^*_{ij-1}$, $Xd^*_{ij}$ and $Xd^*_{ij+1}$, and serve as interpolation points for forming a closed curve curve [sic] in a plane. The values for all planes are formed correspondingly, the result being a spatial illustration.

The information which is contained in an ECG can be illustrated in the above way in three dimensions and in color, the luminance and elasticity being a function of medical facts and not an arbitrary assignment. Such an illustration is comparable to a microscope, which makes available to an observer information which is available and initially withdrawn from direct perception. The small fluctuations within an investigator ECG signal of a "diseased" heart differ from the small fluctuations of a sound heart. These small fluctuations, which were lost in the signal noise in the case of other examination methods are visualized in the above-described method on the basis of medical data. Since the information of an ECG which is available but difficult to interpret is conditioned in a type of topological illustration and permit the smallest deviations to be visualized, the term information microscope is appropriate.

The image data determined as described are conditioned in a control unit 8 for the respective evaluation or display unit, for example a color printer or a monitor, and are thus visualized for the patient or doctor. Of course, such images can be stored or transmitted via datalines.

Figure 13:
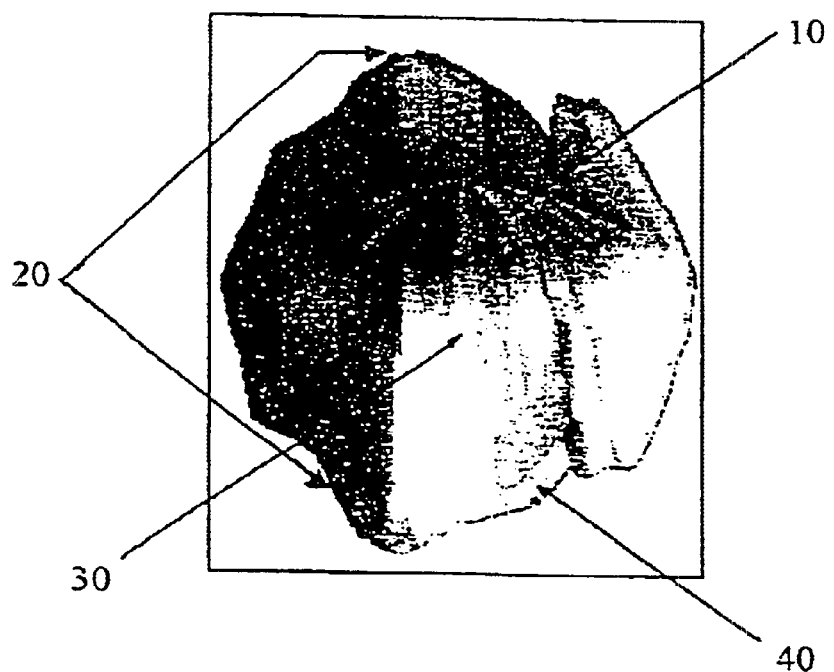
FIG. 13 shows an exemplary illustration of the processed ECG signal.

FIG. 13 shows an exemplary illustration of a processed ECG in its topological form. Various statements can be derived from the shape and color of the respective regions. The region 10 describes the stress level at the instant of measurement. Depending on load, for example owing to physical activity, drugs or addictive substances and/or stimulants, specific variations are formed which are visualized, in particular, by a discoloration.

The regions 20 permit conclusions on the general myocardial function, whereas in the case of severe illnesses the color and the contours of the region 30 change without transition. Functions of the heart chambers are seated in the region 40, and so possible abnormalities or special features are indicated here.

Figure 14:
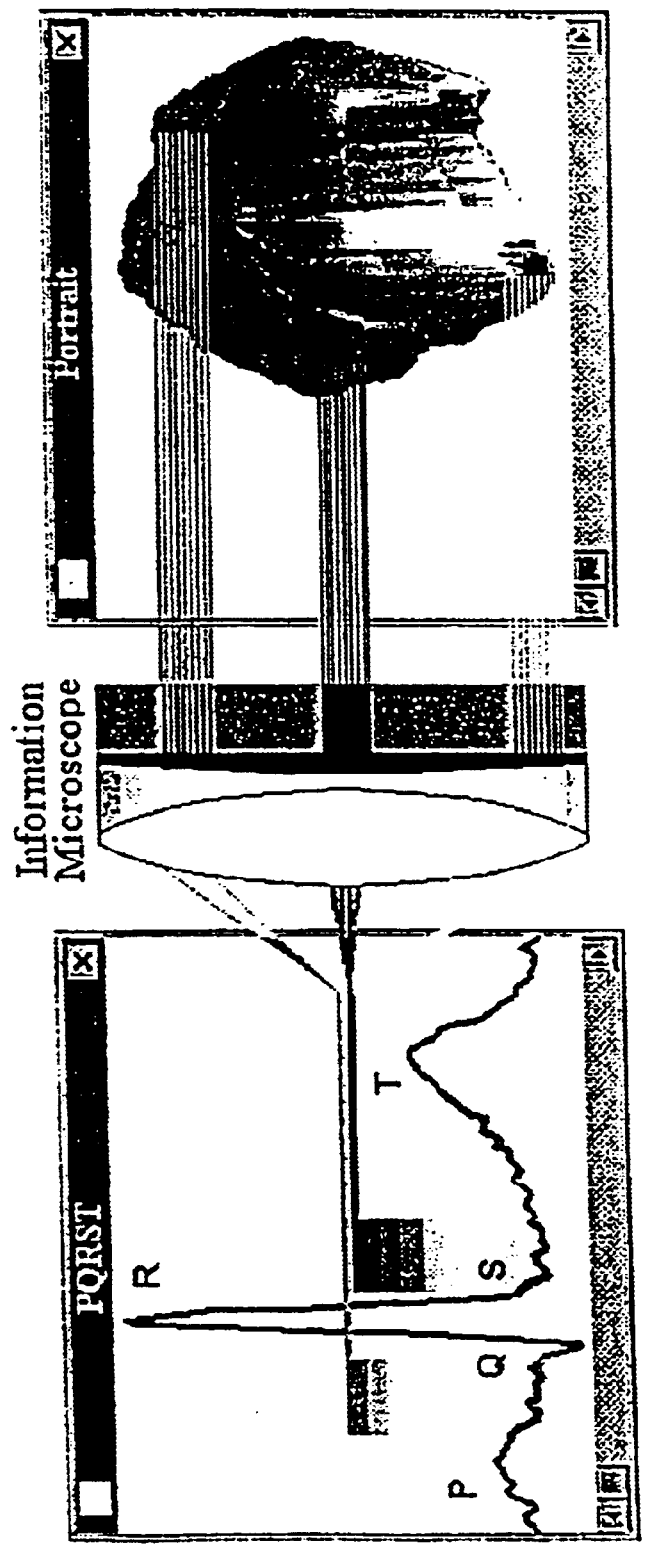
FIG. 14 shows an illustration of the principle of the correspondences between the regions of an ECG and the topological model set up.

FIG. 14 shows an illustration of the principle of the processing of an ECG signal by means of the device according to the invention using the above-described method. The measured ECG signal, illustrated in FIG. 14 on the left in the conventional curve illustration, is generally subdivided into the ranges PQRST. In the method, the stable small fluctuations in the measured signal are evaluated and conditioned in the device denoted as "information microscope", and thus also visualized for the untrained eye. The respective ranges of the curve illustration of an ECG signal are assigned areas on the three-dimensional topological model, which is illustrated in FIG. 14 on the right below the title of "Portrait".

The range about Q, that is to say the auricular systole is located again on the portrait in the area at top right, the range about S is arranged at the left-hand edge, and the ST segment finds its counterpart in the lower area of the portrait.

The device, the "information microscope", is illustrated as a type of magnifying glass, in order to represent its function pictorially. The small fluctuations are detected, processed and "magnified" and a topological model is formed, the so-called portrait, on which, by contrast with the conventional ECG, the variations in and the state of the heart can be read off in a simple way.

Owing to the simple measuring method according to the standardized 3-point recording, and to the fact that evaluation can be carried out simply, it is possible with the aid of this method of representation and with the device according to the invention to carry out in the private sphere a monitoring examination which provides even a layperson with at least guide values for further examinations or treatments.

In the clinical field, the high resolution and the short and informative evaluation mean that it is possible to observe directly the duration of recovery phases after instances of stress, or the effects of drugs. With 6-point recordings there is an increase in the accuracy of the measurement and in the quantity of information, with the result that qualitative and quantitative statements can be made on the state of the heart.

What is claimed is:

1. Method for representing and monitoring cyclical function parameters of electrocardiographic data, which are derived from electronic measuring signals, the data being combined to form a basic data model and being converted into a graphical portrait which is constructed in a three-dimensional topological model, comprising:

fixing an analysis cycle by determining the temporal spacing of at least two repeating significant variables, digitizing the electrocardiographic data acquired during the analysis cycle, feeding the digitized data to a storage unit, assigning a color code and brightness value to the stored digitized data wherein the assignment of the color codes and brightness values are performed according to degree of deviation of the stored digitized data from empirically determined reference data, determining space coordinates from the stored digitized data as surface interpolation points, interpolating the surface interpolation points to generate pixels between the surface interpolation points and generating an essentially closed surface from the pixels, and feeding the essentially closed surface to an evaluation or output device, calculating an autocorrelation function of analysis cycles to be evaluated, comparing the stored digitized data with empirically determined reference data and selecting the analysis cycle to be evaluated in accordance with the comparison, leading the acquired data of an analysis cycle through a high-pass filter, digitizing the filtered acquired data and subtracting the filtered acquired data from unfiltered acquired data, grouping the subtracted data according to a value of the subtracted data, performing a reference measurement to determine a sequence of the group subtracted data, storing a sequence of the for group subtracted data for each physiological system and applying the stored sequence of the group subtracted data to subsequent analysis cycles in order to determine variations in the electrocardiographic data.

2. Method according to claim 1, further comprising determining action potentials in a heart examination using a standardized 3-point recording.

3. Method according to claim 2 further comprising fixing an analysis cycle for determining significant action potentials of a heart muscle over the interval of two R pulses of an electrocardiogram.

4. Method according to claim 1 further comprising determining stored digitized data for generating the essentially closed surface over a time interval which covers a multiple of an analysis cycle.

5. Method according to claim 1 further comprising calling reference data from an electronic memory.

6. Method according to claim 1, wherein generating an essentially closed surface comprises generating an essentially closed surface over all complete analysis cycles of a time interval of the essentially closed surface.

7. Method according to claim 1 by correlation of correlating the acquired data of a plurality of analysis cycles to eliminate noise quantities.

8. Method according claim 1 further comprising transmitting the acquired data to diagnostic centers via data lines.

9. Method according to claim 1 further comprising storing the representation of the essentially closed, surface with a therapy recommendation.

10. Method according to claim 1 further comprising correlating the acquired data of a plurality of analysis cycles to reduce noise quantities.

11. Device for representing and monitoring cyclical function parameters of electrocardiographic data, the device comprising data acquisition means for acquiring the electrocardiographic data and for converting the acquired data into electric signals, a processing unit coupled to the data acquisition means for fixing an analysis cycle as a function of temporal spacing of at least two repeating significant variables, an analog-to-digital converter for digitizing electrocardiographic data acquired within the analysis cycle and having a storage unit for storing the digitized data, an evaluation unit with evaluation software for assigning a color code and brightness value to the digitized data wherein the evaluation unit determines degree of deviation of the stored digitized data from reference data and assigns color codes and brightness values as a function of the degree of deviation, means for determining space coordinates as surface interpolation points;

means for interpolating the interpolation points to generate pixels between the interpolation points;

means for generating an essentially closed surface from the pixels, and means for generating a three-dimensional, colored image with a closed surface on the basis of the acquired data and assigned color code and brightness value, a control unit for conditioning the pixels generated between the interpolation points, and an output unit coupled to the evaluation unit for displaying the colored image, wherein the evaluation unit high pass filters the acquired data of an analysis cycle, digitizes the filtered data and subtracts the digitized filtered data from unfiltered data of the analysis cycle, groups the subtracted data thus obtained according to value of the subtracted data, and feeds a sequence of the group subtracted data to the storage unit, and wherein the evaluation unit applies the sequence of the group subtracted data to subsequent analysis cycles in order to determine variations of the electrocardiographic data, and wherein the evaluation unit calcualtes an autocorrelation function of analysis cycles to be evaluated and compares the autocorrelation function with empirically determined reference data, and wherein the evaluation unit selects the analysis cycle to be evaluated as a function of the comparison.

12. Device according to claim 11, further comprising an interface coupled to the evaluation unit for external data transmission.

13. Device according to claim 11, further comprising an amplifier coupled to the data acquisition means for amplifying the electric signals.

14. Device according to claim 11, wherein the data acquisition means comprise electrodes, pressure sensors, flowrate meters or optical sensors.

* * * * *